United States Patent [19]

Hertl et al.

[11] 4,410,633

[45] Oct. 18, 1983

[54] METHOD FOR THE MEASUREMENT OF FREE THYROXINE OR 3,5,3′-TRIIODOTHYRONINE IN A LIQUID SAMPLE

[75] Inventors: William Hertl, Corning; Frank B. Ward, Painted Post; Howard H. Weetall, Big Flats, all of N.Y.

[73] Assignee: Corning Glass Works, Corning, N.Y.

[21] Appl. No.: 176,654

[22] Filed: Sep. 22, 1980

[51] Int. Cl.$^3$ .................... G01N 33/56; G01N 33/58; G01N 33/60
[52] U.S. Cl. ........................................ 436/500; 435/7; 436/524; 436/527; 436/531; 436/800; 436/804; 436/810
[58] Field of Search .................... 424/1, 12; 23/230 B; 435/7; 436/500, 524, 527, 531, 800, 804, 810

[56] References Cited

U.S. PATENT DOCUMENTS

| | | | |
|---|---|---|---|
| 4,046,870 | 9/1977 | Hertl et al. | 424/1 |
| 4,225,574 | 9/1980 | Romelli et al. | 424/1 |
| 4,235,865 | 11/1980 | Thoma | 424/1 |
| 4,243,749 | 1/1981 | Sadeh et al. | 424/12 |
| 4,289,748 | 9/1981 | Harris et al. | 424/12 |
| 4,311,690 | 1/1982 | Buehler et al. | 424/1 |

FOREIGN PATENT DOCUMENTS 26103  4/1981  European Pat. Off. ................. 424/1

OTHER PUBLICATIONS

R. F. Schall, Jr. et al., *Clin. Chem.*, 24, 1801, (1978).
G. Kleinhammer et al., "Enzyme Immuno Assay for Determination of the Thyroid Binding Index," unpublished text of published abstract.
Kleinhammer & Schall, Jr. et al., Clin. Chem., vol. 24, No. 6, 1978, p. 1033.

*Primary Examiner*—Christine M. Nucker
*Attorney, Agent, or Firm*—W. E. Maycock

[57] ABSTRACT

An immunoassay for the measurement of free thyroid hormone, i.e., thyroxine or 3,5,3′-triiodothyronine, in a liquid sample in which the thyroid hormone is present in both free and combined states, which immunoassay comprises the steps of:

A. combining the sample with a labeled thyroid hormone-horseradish peroxidase conjugate which does not significantly interact with the thyroxine-binding globulin and thyroxine-binding prealbumin originally present in the sample and immobilized antibody which is specific for the thyroid hormone;
B. incubating the resulting mixture;
C. separating a solid phase from the liquid phase; and
D. measuring the amount of labeled thyroid hormone-horseradish peroxidase conjugate present in either phase by means of the activity of the label.

15 Claims, 6 Drawing Figures

METHOD FOR THE MEASUREMENT OF FREE THYROXINE OR 3,5,3'-TRIIODOTHYRONINE IN A LIQUID SAMPLE

BACKGROUND OF THE INVENTION

The present invention relates to a method for the measurement of free thyroxine or free 3,5,3'-triiodothyronine in a liquid sample in which the thyroxine or 3,5,3'-triiodothyronine is present in both free and combined states. The method utilizes a labeled thyroxine or 3,5,3'-triiodothyronine-horseradish peroxidase conjugate which does not significantly interact with the thyroxine-binding globulin and thyroxine-binding prealbumin originally present in the sample.

It frequently is necessary to determine the concentration of free thyroxine in a liquid sample in which the thyroxine is present in both free and combined or bound states. Typically, such a determination is part of a routine hematological examination of blood serum or plasma for the prophylaxis or treatment of a variety of disorders and diseases.

Thyroxine and 3,5,3'-triiodothyronine (hereinafter, triiodothyronine) are characteristic hormones, secreted by the thyroid, which have profound physiological effects on the basal metabolic rate of mammals. While triiodothyronine exhibits greater hormonal activity than thyroxine, it appears that thyroxine is the principal circulating thyroidal hormone. Thus, the comments which follow concentrate on thyroxine but also are generally applicable to triiodothyronine.

Thyroxine is stored in the thyroid gland as thyroglobulin, a glycoprotein, and is released via proteolysis. In the blood, thyroxine is largely bound to plasma proteins, primarily thyroxin-binding globulin and thyroxine-binding prealbumin. A small but finite amount of thyroxine is free or unbound, and it is this free thyroxine which is the physiologically-active entity. Thus, the determination of free thyroxine in the blood is an important part of the diagnosis of thyroid dysfunction.

The primary problem associated with any assay for free thyroxine is the fact that free thyroxine is present in human serum at very low concentrations. The accepted normal range is from about 0.8 to about 2.5 ng. of free thyroxine per dl. of serum (8-25 pg./ml.). This range typically is much less than about 1% of the total thyroxine normally present in serum and requires accurate measurements in parts per trillion.

Free thyroxine has been determined via equilibrium dialysis, a time-consuming and operator-intensive method. In addition, there are two known immunoassays for the measurement of free thyroxine. The first (Corning Medical and Scientific Division, Corning Glass Works, Medfield, Mass.) is a two-tube method which measures the rate of transfer of thyroxine from the binding proteins to the thyroxine-specific antibody. This method, which is discussed in greater detail below, requires carefully timing the antigen pick-up by the antibody in two separate tubes. The second method (Clinical Assays Division, Travenol Laboratories, Inc., Deerfield, Ill.) employs a single tube in which the thyroxine-specific antibody is incubated with the sample for a precisely-controlled period of time; the amount of antigen picked up by the antibody is related to the free thyroxine originally present. The antibody-antigen complex is separated from the sample and then is incubated with radiolabeled thyroxine which complexes with unoccupied binding sites on the antibody. Thus, the amount of radio-activity picked up by the complex is inversely proportional to the concentration of free thyroxine originally present in the sample.

The first method above is essentially taught by U.S. Pat. No. 4,046,870 which discloses a method for determining the concentration of free thyroid hormone in a blood serum sample which comprises the steps of analyzing the sample by immunoassay (typically radioimmunoassay) for the desired thyroid hormone in the presence and absence of a blocking agent such as merthiolate (thimerosal) or 8-anilino-1-naphthalenesulfonic acid to establish a thyroid hormone binding differential and then correlating that differential with a standard curve relating the respective free thyroid hormone concentrations to binding differentials.

There still is a need, however, for a rapid, sensitive, and accurate procedure for the direct measurement of free thyroxine in a liquid sample in which the thyroxine is present in both free and combined states. Such a need now has been met through the discovery that a labeled thyroxine-horseradish peroxidase conjugate which does not significantly interact with the thyroxine-binding globulin and thyroxine-binding prealbumin originally present in the sample can be utilized in an immunoassay to permit the measurement of free thyroxine in the sample. Because the horseradish peroxidase in the conjugate substantially retains its activity when complexed with an immobilized antibody which is specific for thyroxine, the conjugate is particularly well suited for a thyroxine solid-phase enzyme immunoassay.

In general, hapten-enzyme conjugates are well known in the prior art. See, for example, U.S. Pat. Nos. 3,654,090; 3,791,932; 3,839,153; 3,850,752; 3,879,262; 4,016,043; 4,040,907; and Re. 26,169. Several of these patents are of particular interest.

U.S. Pat. No. 3,839,153 discloses an enzyme immunoassay which utilizes a double antibody approach. Thus, a hapten (or antigen)-enzyme conjugate and soluble antibody specific for the hapten (or antigen) are mixed with the sample to be tested. An insolubilized antibody then is added to the reaction mixture, wherein the insolubilized antibody is specific for the soluble antibody previously employed. The resulting insolubilized antibody-antibody-hapten (or antigen)-enzyme complex then is separated from the mixture and the enzymatic activity of either separated phase is determined. Peroxidase is included in the examples of suitable enzymes, although there is no suggestion that the procedure is suitable for the determination of thyroxine in a sample, and certainly not for free thyroxine.

U.S. Pat. No. 3,850,752 also relates to enzyme immunoassays. Briefly, the patent teaches a process for the determination of a hapten which involves adding to the sample to be tested a hapten-enzyme conjugate and an insolubilized antibody specific for the hapten. The resulting insolubilized antibody-hapten-enzyme complex then is separated from the mixture and the enzyme activity of either resulting phase is determined. Peroxidase is included in the examples of suitable enzymes and thyroxine is included in the examples of haptens which can be determined by the disclosed method. There is, however, no specific teaching of a thyroxine-peroxidase conjugate or of the determination of free hapten, e.g. thyroxine.

U.S. Pat. No. 3,879,262 also relates to enzyme immunoassays. The disclosed process actually amounts to an improvement of each of the processes of U.S. Pat. Nos.

3,839,153 and 3,850,752. Such improvement requires that the nature of the coupling between hapten and enzyme differs from the coupling between hapten and an immunogenic material, the latter conjugate being used to produce hapten-specific antibodies in an animal. Thyroxine is included in the list of suitable haptens and peroxidases are included in the list of suitable enzymes. There is no specific teaching of a thyroxine-peroxidase conjugate however. Furthermore, the disclosed process is not used to determine free hapten.

Finally, U.S. Pat. No. 4,040,907 relates to polyiodothyronine or thyroxine conjugates with enzymes. The enzymes in such conjugates must undergo substantial change in activity to be useful in enzyme immunoassays.

Two additional references are known which disclose thyroxine-peroxidase conjugates. The first is R. F. Schall, Jr. et al., Clin. Chem., 24, 1801 (1978); an abstract of the paper appeared in Clin. Chem., 24, 1033 (1978). This reference discloses a manual enzyme immunoassay for thyroxine. The procedure determines total thyroxine in serum and is carried out as follows: The serum sample is mixed with the thyroxine-horseradish peroxidase conjugate solution which also contains a blocking agent, 8-anilino-1-naphthalene-sulfonic acid, and immobilized antibody specific for thyroxine. The resulting mixture is incubated and centrifuged. The solid phase is washed and a substrate-chromogen solution is added to the solid phase. Color is allowed to develop and then is fixed. Absorbance is measured and total thyroxine content of the sample is determined from a standard curve.

The second additional reference is G. Kleinhammer et al., "Enzyme Immuno Assay for Determination of the Thyroid Binding Index", a paper presented at the annual meeting of the American Association for Clinical Chemistry, July 1978; an abstract was published in Clin. Chem., 24, 1033 (1978). According to the paper, the first attempts to develop an enzyme immunoassay able to recognize abnormal thyroxine-binding globulin (TBG) concentrations were unsuccessful, primarily because the thyroxine-horseradish peroxidase conjugate failed to bind to TBG. The assay as reported is carried out as follows: To a serum sample is added a fixed amount of thyroxine, which amount is in excess of unbound TBG in the sample. The amount of excess thyroxine not bound by TBG is measured by enzyme immunoassay using thyroxine-horseradish peroxidase and tubes coated with antibody specific for thyroxine. Thus, the procedure was not employed to determine free thyroxine in the serum. Because the trilodo-thyronine-horseradish peroxidase conjugate also failed to bind to TBG, such conjugate can be used in place of the thyroxine-horseradish peroxidase conjugate, although the latter was preferred because of the higher binding affinity of TBG for thyroxine.

It should be noted that specific enzyme immunoassays for total thyroxine are known. Such assays are based on either malate dehydrogenase or alkaline phosphatase; see, e.g., P. R. Finley and R. J. Williams, Clin. Chem., 24, 165 (1978); A. P. Jaklitsch et al., Clin. Chem., 21, 1011 (1975); F. VanLente and D. J. Fink, Clin. Chem., 24, 387 (1978); R. S. Galen and D. Forman, Clin. Chem., 23, 119 (1977); and Japanese Pat. No. 77/108017.

SUMMARY OF THE INVENTION

It therefore is an object of the present invention to provide an enzyme immunoassay for free thyroxine in a liquid sample in which the thyroxine is present in both free and combined states.

It also is an object of the present invention to provide a nonenzyme immunoassay for the measurement of free thyroxine in a liquid sample in which the thyroxine is present in both free and combined states.

A further object is to provide an enzyme immunoassay for free triiodothyronine in a liquid sample in which the triiodothyronine is present in both free and combined states.

Another object is to provide a nonenzyme immunoassay for the measurement of free triiodothyronine in a liquid sample in which the triiodothyronine is present in both free and combined states.

These and other objects will be apparent to those skilled in the art from a consideration of the specification and claims which follow.

Accordingly, the present invention provides an immunoassay for the measurement of free thyroxine in a liquid sample in which the thyroxine is present in both free and combined states, which immunoassay comprises the steps of:

A. combining the sample with a labeled thyroxine-horseradish peroxidase conjugate which does not significatly interact with the thyroxine-binding globulin and thyroxine-binding prealbumin originally present in the sample and immobilized antibody which is specific for thyroxine;

B. incubating the resulting mixture;

C. separating a solid phase from the liquid phase; and

D. measuring the amount of labeled thyroxine-horseradish peroxidase conjugate present in either phase by means of the activity of the label.

The present invention also provides an immunoassay for the measurement of free triiodothyronine in a liquid sample in which the triiodothyronine is present in both free and combined states, which immunoassay comprises the steps of:

A. combining the sample with a labeled triiodothyronine-horseradish peroxidase which does not significantly interact with the thyroxine-binding globulin and thyroxine-binding prealbumin originally present in the sample and immobilized antibody which is specific for triiodothyronine;

B. incubating the resulting mixture;

C. separating a solid phase from the liquid phase; and

D. measuring the amount of labeled triiodothyronine-horseradish peroxidase conjugate present in either phase by means of the activity of the label.

BRIEF DESCRIPTION OF THE DRAWINGS

FIG. 6 demonstrates the binding affinities of $^{125}I$-thyroxine and $^{125}I$-thyroxine-bovine serum albumin conjugate for thyroxine-binding globulin.

DETAILED DESCRIPTION OF THE INVENTION

As used herein, the terms "insolubilized" and "immobilized" are synonymous and require only substantial insolubility in aqueous media.

For convenience in the discussion which follows, the term "hapten-horseradish peroxidase conjugate", including variations thereof, is meant to include both thyroxine-horseradish peroxidase conjugate and triiodothyronine-horseradish peroxidase conjugate.

It will be apparent to those having ordinary skill in the art that, regardless of the nature of the label in the labeled hapten-horseradish peroxidase conjugate, it is necessary to couple hapten to horseradish peroxidase. Furthermore, where the label is not horseradish peroxidase per se, either or both of the hapten and horseradish peroxidase moieties can be labeled before or after the preparation of the conjugate. Thus, the preparation of the conjugate can be viewed as involving (a) the coupling of hapten to horseradish peroxidase and (b) optionally inserting a label other than horseradish peroxidase into the conjugate before or after (a), both steps being carried out by well-recognized procedures which are known to those having ordinary skill in the art. By way of illustration only, general descriptions of hapten-enzyme coupling procedures are found in U.S. Pat. Nos. 3,839,153; 3,850,752; 3,879,262, and 4,040,907.

Suitable labels for the hapten-horseradish peroxidase are conveniently divided into two general categories: enzymatic labels and nonenzymatic labels.

Enzymatic labels, of course, obviously include horseradish peroxidase since the enzyme retains substantial enzymatic activity when coupled with the hapten. Other enzymes, however, also can be present in the hapten-horseradish peroxidase conjugate, with the enzymatic activity of interest being that of such other enzymes. As with the preparation of the hapten-horseradish peroxidase conjugate, the coupling of an enzyme other than horseradish peroxidase is accomplished by methods well known in the art.

In general, the nonenzymatic label can be any label known to those skilled in the art. Thus, the conjugate can be radiolabeled, fluorescent-labeled, chemiluminescent-labeled, or the like. While labeling techniques typically are well-known, several of the more widely-used procedures are discussed briefly.

The procedure of choice in the preparation of a radiolabeled hapten-horseradish peroxidase conjugate to a large extent is dependent upon the radioactive isotope which is to be employed. Examples of the more suitable of such isotopes include, among others, $H^3$, $C^{14}$, $S^{35}$, $I^{125}$, and $I^{131}$, with $I^{125}$ and $I^{131}$ being most preferred.

In general, any of the known fluorescent labels can be employed in the preparation of a fluorescent-labeled conjugate. Examples of suitable fluorescent labels include, among others, fluorescein isothiocyanate, tetraethylrhodamine, fluorescamine, and the like. Of course, the preparative procedure selected in any given case is dependent, at least in part, upon the structure of the fluorescent label. Typically, however, the fluorescent label can be covalently bound in accordance with standard procedures to either the hapten or the horseradish peroxidase. Alternatively, the fluorescent label can be coupled to either moiety via an intermediate coupling agent such as a polypeptide.

Similar principles are involved in the preparation of a chemiluminescent-labeled conjugate. Suitable chemiluminescent labels inlude, among others, luminol, luciferin, lucigenin, acridine, pyrogallol, indole, riboflavin, lophine, methylene blue, siloxene, and the like.

It should be apparent to one skilled in the art that regardless of the nonenzymatic label used or the particular method employed to prepare the labeled conjugate, the label must retain its intended function without impairing either the ability of the hapten to bind to the anti-hapten antibody or the noninteraction characteristic of the conjugate.

The preparation of the complex of a labeled hapten-horseradish peroxidase conjugate with immobilized antibody specific for the hapten is carried out in accordance with known procedures. In practice, it is only necessary to bring the conjugate and immobilized antibody together in an aqueous medium.

In general, antibody specific for hapten is generated in accordance with known procedures. Typically, however, the antiserum thus obtained is not further processed to give purified antibody. As a matter of convenience, the immobilized antibody is prepared directly from the antiserum. Thus, the immobilized antibody preparation inevitably has associated with it immobilized proteins, e.g., globulins, of various types, none of which are significant with respect to the present invention. Accordingly, the term "immobilized antibody" does not require any particular degree of purity, although it will be apparent to those skilled in the art that immobilized antibody preparations derived directly from antiserum will require more of such preparation per unit of hapten than such a preparation derived from purified antiserum.

The immobilization of antibody in turn is carried out in accordance with well known procedures. In general, neither the carrier nor the immobilization procedure is critical, provided that significant deleterious effects are avoided. Thus, the carriers can be organic or inorganic, porous or nonporous, and in any desired shape or form. The carrier can be particulate in nature, varying from a finely-divided powder to a coarse granular material, or the carrier can be a continuous, shaped article such as a flat or curved sheet or pellet, or a three-dimensional article such as a rectangular or cylindrical tube or a complex monolith. As a practical matter, the carrier most often will be either particulate and relatively finely divided, e.g., from about 20 to about 100 mesh, U.S. Standard Sieve, or a three-dimensional article, e.g., a cylindrical tube closed at one end, i.e., a test tube.

Examples of suitable organic carriers include, among others, polyesters, such as poly(ethylene terephthalate); polyamides, such as nylon 6 and nylon 6.6; polyacrylates; polymethacrylates; polyacrylamides; poly(acrylic acid); poly(methacrylic acid); poly(galacturonic acid); poly(aspartic acid); ethylene-maleic anhydride copolymers; polylefins, such as polyethylene, polypropylene, polybutene, and polybutadiene; polystyrene; poly(aminostyrene); poly(vinyl chloride); poly(vinyl alcohol); poly(vinylidine chloride); cellulose; agarose gels; dextran gels; polysaccharides; polypeptides; collagen; and the like.

The inorganic carriers can be classified as siliceous or nonsiliceous metal oxides. Examples of siliceous carriers include, among others, glass, silica, wollastonite, bentonite, cordierite, and the like. Examples of nonsiliceous metal oxides include, among others, alumina, spinel, apatite, nickel oxide, titania, zirconia, and the like.

The preferred particulate carriers are inorganic in nature, with siliceous materials being more preferred.

The most preferred carriers are silica and glass. Preferably, the carrier will be porous in order to provide a greater amount of antibody per unit volume or mass of carrier. Furthermore, the carrier surface can be modified by methods well known in the art, such as by etching or frosting, chemical treatment, chemical coating, and the like.

When the carrier is a three-dimensional article such as a test tube, the carrier preferably is a plastic such as polyethylene or polypropylene. Thus, a more preferred embodiment of the use of a three-dimensional article is a plastic test tube antibody coated on the lower interior portion thereof.

In general, the antibody can be immobilized by any known means which can vary from simple adsorption to chemical coupling. Adsorption, of course, usually involves contacting an aqueous solution of the antibody (antiserum) to be immobilized with the carrier for a time sufficient to permit the desired (or maximum) degree of immobilization. Chemical coupling typically involves treating the carrier with one or more chemical compounds, followed by contacting the treated carrier with an aqueous solution of the antibody. Among the chemical compounds which can be used to treat the carrier, and especially the inorganic carrier, are o-dianisidine (U.S. Pat. No. 3,983,000), polymeric isocyanates (U.S. Pat. No. 4,071,409), silanes (U.S. Pat. Nos. 3,519,538, 3,652,761, and 3,669,841), and the like. See also U.S. Pat. Nos. 3,930,951 and 3,933,589. For examples of procedures suitable for the immobilization of antibodies to inorganic carriers, see U.S. Pat. No. 4,034,073; M. K. Weibel at al., *Biochem. Biophys. Res. Comm.*, 44, 347 (1971); and H. H. Weetall, *Science*, 166, 615 (1969).

It will be apparent to those skilled in the art that the enzyme immunoassay and nonenzyme immunoassay disclosed herein are in fact very similar, differing primarily in the method employed to determine or measure the amount of conjugate present, which method is dependent upon the nature of the label incorporated into the conjugate. Thus, the parameters which pertain to the methodology can be discussed generally, it being understood that such parameters apply to both the enzyme and nonenzyme immunoassays. Consequently, the term "conjugate" is used throughout such discussion without reference to any particular label.

The first step in either of such immunoassays comprises combining the sample with conjugate which does not significantly interact with the thyroxine-binding globulin and thyroxine-binding prealbumin originally present in the sample and immobilized antibody which is specific for the hapten.

The amount of conjugate employed is not critical, although to maximize the sensitivity of the immunoassay the amount of conjugate added preferably will provide an amount of free conjugate which is approximately equivalent, on a molar basis, to the amount of free hapten originally present in the sample.

Similarly, the amount of immobilized antibody employed is not critical, provided that such amount is not sufficient to remove a significant proportion of the bound hapten from the binding proteins. That is, the immobilized antibody should be present in an amount sufficient to bind a proportion of free hapten which is sufficient to provide adequate sensitivity during the measuring step. In practice, the proper amount of immobilized antibody is readily determined by one having ordinary skill in the art and is dependent, at least in part, on the titer of the antiserum and the extent or degree of antibody immobilization. With respect to the immunochemical reaction between hapten and the immobilized antibody, it should be noted that the term "free hapten" necessarily refers to all hapten which is not in a bound state, i.e., which is not bound to thyroxine-binding globulin and thyroxine-binding prealbumin, among other proteins, originally present in the sample. Thus, the term "free hapten" includes all hapten which is capable of being bound to or complexed with anti-hapten antibody, and, as a consequence, includes both free hapten originally present in the sample and hapten subsequently added to the sample in the form of the conjugate. It follows, then, that the term "labeled hapten" simply refers to hapten present as the conjugate.

The second step comprises incubating the mixture resulting from the first step, preferably for a time sufficient to achieve or closely approach equilibrium binding. In general, incubation can be at any temperature which is not destructive of the components of the mixture. Typically, the incubation temperature will be in the range of from about ambient temperature to about 40° C. Incubation times are not critical. As already indicated, it is preferred that such times be sufficient to achieve or closely approach equilibrium binding. Normally, incubation times of about an hour at 37° C. are sufficient although longer or shorter times often can be employed.

The third step comprises separating a solid phase from the liquid phase. Such separation can be carried out by any known means. For example, with a particulate carrier, such separation can be achieved by filtration or centrifugation, with centrifugation being preferred for speed and convenience. When the carrier is a three-dimensional article such as a test tube, such separation can be achieved by simply decanting or aspirating the liquid phase from the tube.

The solid phase, of course, irrespective of carrier configurtion, consists of immobilized antibody and/or immobilized antibody-hapten complex. Further, it is apparent that the complex can contain hapten from two sources: (1) free hapten which was originally present in the sample, and (2) hapten in the form of the conjugate. Indeed, the success of the method depends upon the presence in the complex of hapten from both sources, since there is competition by hapten from both sources for a limited number of antibody binding sites. By keeping the amounts of conjugate and immobilized antibody constant, the amount of hapten from the second source present in the complex is inversely proportional to the amount of hapten from the first source, i.e., free hapten originally present in the sample.

The fourth step comprises measuring the amount of conjugate present in either phase. Preferably, the amount of conjugate present in the solid phase will be measured. Clearly, the method of measurement will depend upon the nature of the conjugate. An integral part of the measurement step is the correlation of the amount of conjugate present on the immobilized antibody with a standard curve which relates the amount of conjugate present to the concentration of free hapten originally present in the sample. The preparation of the standard curve is done in accordance with well-known procedures and is well within the knowledge of one having ordinary skill in the art.

The present invention is further illustrated, but not limited, by the examples which follow. Unless otherwise stated, all temperatures are in degrees celsius.

EXAMPLE 1

Determination of Free Thyroxine in Human Serum Samples Via Enzyme Immunoassay Utilizing Antibody Immobilized on a Particulate Carrier Materials and Reagents 1. Free thyroxine standards were prepared from Corning's kinetic free thyroxine assay (IMMO PHASE ™ Free Thyroxine Radioimmunoassay, Corning Medical, Medfield, Mass.). Such standards were serum based and included 0.5, 1, 2, 4, and 6 ng. of free thyroxine, respectively, per dl. of serum.

2. Anti-thyroxine antibody was obtained by the immunization of New Zealand white rabbits. The resulting antiserum had a titer of about 1:50,000.

3. The carrier used for antibody immobilization was the arylamine derivative of silanized controlled-pore glass. The average particle size was about 1μ with an average pore diameter of about 550Å. Immobilized antiserum (immobilized antibody, IMA) was prepared according to Weetall and Filbert, using a ratio of 0.5 gram of glass per ml. of antiserum; see W. B. Jakoby and M. Wilchek, Editors, "Methods in Enzymology", Volume 34B, Academic Press, Inc., New York, 1974, p. 59–72. Briefly, the glass was cleaned in 5% nitric acid solution, washed, and treated with a 10% solution of γ-aminopropyltriethoxysilane in distilled water at a pH of 3.45. The resulting silanized glass was reacted with p-nitrobenzoyl chloride in chloroform containing 10% (v/v) triethylamine as a hydrogen chloride scavenger. Reduction of the nitro group then was accomplished by treating the p-nitrobenzoylaminoalkyl derivatized glass with 10% sodium dithionite in water. The resulting p-aminobenzoylaminoalkyl derivatized glass was diazotized with nitrous acid generated in situ from hydrochloric acid and sodium nitrite. The diazotized product was washed and added to antiserum at pH 8–9. The resulting IMA was washed repeatedly and resuspended in buffer. The resulting IMA suspension contained 50 mg of glass per ml. and about 50 μg of IMA per ml.

4. The conjugate used was thyroxine-horseradish peroxidase (Organon Diagnostics, El Monte, Calif.).

5. The buffer employed in all experiments was pH 7.4 0.03 M sodium phosphate containing 0.1% bovine serum albumin.

6. The enzyme substrate solution composition was as follows: 0.033 M citric acid, 0.066 M sodium phosphate, 0.0065 M o-phenylenediamine dihydrochloride, and 0.0021 M urea peroxide; the buffer pH was 5.0±0.1.

7. The color development stopping solution was 1.0 M citric acid containing 0.1% sodium azide.

8. The IMA washing solution contained 0.05% TWEEN ™ 80 (Fisher Scientific Co., Pittsburgh, Pa.) in 0.85% aqueous sodium chloride solution.

9. Human serum samples were obtained from Metpath and a local gynacologist. All samples were first analyzed for free and total thyroxine by prior-art methods (i.e., equilibrium dialysis and radioimmunoassay).

Preparation of Standard Curve

Figure 1:
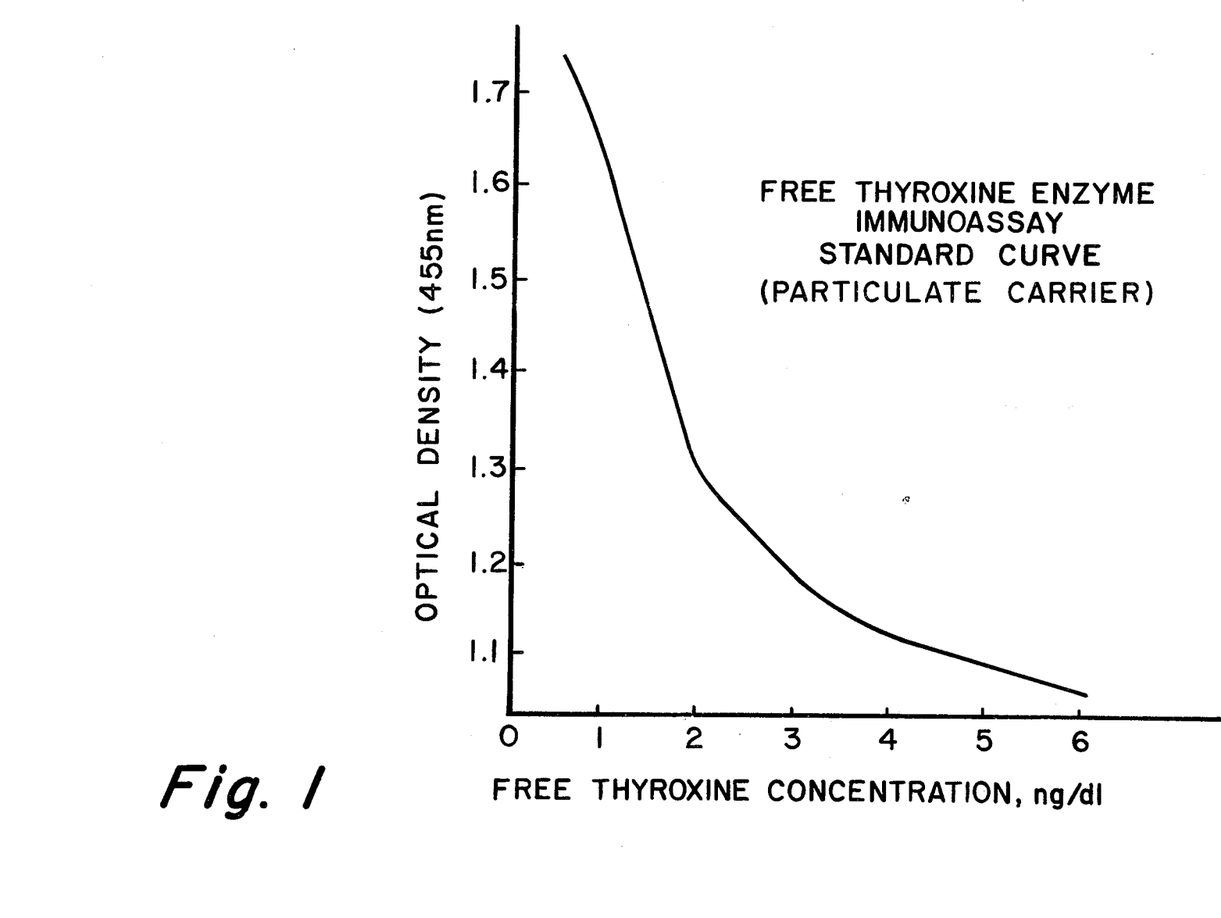
FIG. 1 is a free thyroxine enzyme immunoassay standard curve obtained with anitbody immobilized on a particulate carrier.

To 20 μl. of each thyroxine standard in a separate 12×75 mm. plastic test tube was added 0.1 ml. of conjugate (about 200 pg. of thyroxine by radioimmunoassay). To the resulting mixture was added 1 ml. (about 50 μg) of IMA. The mixture was incubated for 30 minutes at 37°. The mixture was centrifuged and the solid phase was washed twice by each time adding 2 ml. of wash solution, vortexing, and centrifuging for five minutes at about 3,000 RPM. To the washed solid phase then was added, on a timed schedule, with mixing, 2 ml. of enzyme substrate solution. After a precise 15-minute incubation period at ambient temperature, color development was terminated by the addition of 1 ml. of stopping solution. The optical density at 455 nm. of each solution was determined spectrophotometrically. The data thus obtained were plotted as optical density vs. free thyroxine concentration in ng./dl. See FIG. 1 which clearly shows that the assay is sensitive to small changes in free thyroxine concentration over the range of from about 0.5 to about 6 ng/dl.

Assay of Human Serum Samples

The procedure employed to generate the data for the standard curve was repeated, except that each thyroxine standard was replaced with a human serum sample (in duplicate). The optical density reading obtained in each case was correlated with the standard curve to obtained a free thyroxine concentration. The data thus obtained are summarized in Table I which also tabulates the previously-determined free thyroxine values.

TABLE I

Free Thyroxine Values of Human Serum Samples (ng./dl.)

| Sample No. | Present Method | Prior-Art Method |
|---|---|---|
| 2-B | 1.7 | 1.4 |
| 4-B | 2.4 | 2.4 |
| 6-A | 2.4 | 2.0 |
| 8-A | 1.8 | 1.4 |
| 9-A | 1.4 | 1.3 |
| 10-A | 1.8 | 1.8 |
| 13-A | 1.6 | 1.5 |
| 14-A | 2.1 | 2.2 |
| A-2 | 2.0 | 1.7 |
| A-13 | 2.5 | 2.2 |
| A-14 | 2.2 | 2.2 |
| A-15 | 1.6 | 2.1 |
| A-17 | 2.5 | 2.2 |

Evaluation of Binding Constants

A measure of how strongly an antigen or hapten is bound to an antibody is given by the value of the equilibrium or binding constant which is defined as follows:

$$K = \frac{[Ag/Ab]}{[Ag][Ab]}$$

where
K = the equilibrium or binding constant
[Ag/Ab] = the concentration of the antigen (or hapten)-antibody complex
[Ag] = the concentration of free or unbound antigen (hapten)
[Ab] = the concentration of free or unbound antibody Clearly, the greater the value of K, the more strongly antigen is bound to antibody. If the bound and free antigen can be separated and the quantity bound measured, then the value of K can be determined by constructing a Scatchard plot; see, e.g., E. D. Day, "Advanced Immunochemistry", Williams & Wilkens Co., Baltimore, Md., 1972, pp. 118ff. Such a procedure is particularly suited to solid-phase immunoassay systems since the bound antigen is readily separated from the free or unbound antigen.

For the thyroxine-horseradish peroxidase conjugate, the value of K was determined as follows. A stock solution of the conjugate was assayed for total thyroxine by means of a conventional radioimmunoassay to give the concentration of the thyroxine-horseradish peroxidase conjugate. A quantity of the immobilized antibody used hereinabove was added to an aliquot of the conjugate stock solution and the resulting mixture was incubated. The solid phase then was separated by centrifugation. The liquid phase was assayed for total thyroxine as before. The difference between the two concentrations of thyroxine-horseradish peroxidase conjugate represents the amount of conjugate which was complexed by the immobilized antibody. The immobilized antibody, or solid phase, in turn was assayed by the colorimetric procedure described hereinabove which results in an optical density value which is attributable to the known amount of conjugate bound to the immobilized antibody. This enables the amount of bound conjugate to be expressed in terms of optical density units. Various dilutions of this stock solution then were added to a series of tubes containing identical quantities of IMA. The resulting mixtures were incubated for one hour and centrifuged. The supernatant liquid was decanted and the quantity of conjugate bonded or complexed to the IMA was determined by the colorimetric procedure already described. From the quantity bound and the known total amount added initially, the fraction of conjugate which was bonded to the IMA was calculated for each dilution. The values necessary for the Scatchard plot are given in Table II.

TABLE II

Thyroxine-Horseradish Peroxidase Conjugate Scatchard Plot Data

| Dilution of Stock Soln. | Fraction Bound/Free | Amount Bound $\times 10^{13}$ Moles |
|---|---|---|
| Series I[a] | | |
| 1:1000 | 0.023 | 0.50 |
| 1:500 | 0.021 | 0.91 |
| 1:250 | 0.018 | 1.52 |
| 1:125 | 0.013 | 2.28 |
| 1:62.5 | 0.0085 | 2.95 |
| 1:31.2 | 0.0059 | 4.10 |
| 1:16 | 0.0032 | 4.45 |
| Series II[b] | | |
| 1:1000 | 0.0089 | 0.18 |
| 1:500 | 0.0077 | 0.32 |
| 1:250 | 0.0063 | 0.52 |
| 1:125 | 0.0066 | 1.09 |
| 1:62.5 | 0.0055 | 1.68 |
| 1:31.2 | 0.0051 | 3.38 |
| 1:16 | 0.0036 | 4.7 |

[a]Series I was carried out in the absence of added human serum protein.
[b]Series II was carried out in the presence of added human serum protein.

The data in Table II were plotted with the second column data as ordinate and the third column data as abscissa. The resulting plots were essentially linear, the slopes of which were equal to K. Thus, the binding constants from the above data, as well as the constant for a nonconjugated thyroxine (data not shown), were as follows:

| | K |
|---|---|
| Thyroxine-horseradish peroxidase conjugate, Series I | $6 \times 10^{10}$ |
| Thyroxine-horseradish peroxidase conjugate, Series II | $7.2 \times 10^{10}$ |
| Free thyroxine[a] | $3 \times 10^{10}$ |

[a]In merthiolate-containing human serum.

The differences in the above values of K are not experimentally significant. Thus, the data clearly show that the affinity of the conjugate for specific immobilized antibody, even in the presence of serum containing thyroxine-binding globulin, is not significantly different from the affinity of nonconjugated thyroxine for the same antibody, which free thyroxine was prevented by the presence of a blocking agent from binding to thyroxine-binding globulin present in the serum.

Conjugate Noninteraction with Serum Protein

Obviously, the foregoing values of K indicate the noninteraction characteristic of the thyroxine-horseradish peroxidase conjugate. The following experiment, however, was designed to demonstrate such noninteraction and to compare the TBG binding characteristic of conjugate with that of free or nonconjugated thyroxine.

A stock solution of purified TBG was serially diluted, in duplicate, in 12×75 mm. plastic test tubes. Thus, two identical series of six tubes each, A and B, were prepared, with each tube containing 100 l. of solution. The six tubes in each series contained, respectively, 10 $\mu$g, 1 $\mu$g, 100 ng, 10 ng, and zero TBG. To each tube then was added 1 ml. of buffer containing 200 $\mu$g of IMA. In addition, each tube in Series A also received 100 $\mu$l of $^{125}$I-labeled thyroxine (Stock No. 474119-A, Corning Medical) and each tube in Series B received 100 $\mu$l of conjugate. All tubes were incubated at 37° for one hour. All tubes then were centrifuged and in each case the solid phase was washed twice as already described. The amount of thyroxine contained in the solid phase of each tube in Series A was determined by measuring the gamma radiation therein and the data recorded as counts per minute. By using an appropriately-constructed standard curve, such data were converted to the fraction of thyroxine bound in each tube. The amount of thyroxine contained in the solid phase of each tube in Series B was determined colorimetrically as already described. Again, by using a suitable standard curve, the data were converted to the fraction of thyroxine bound in each tube.

Figure 2:
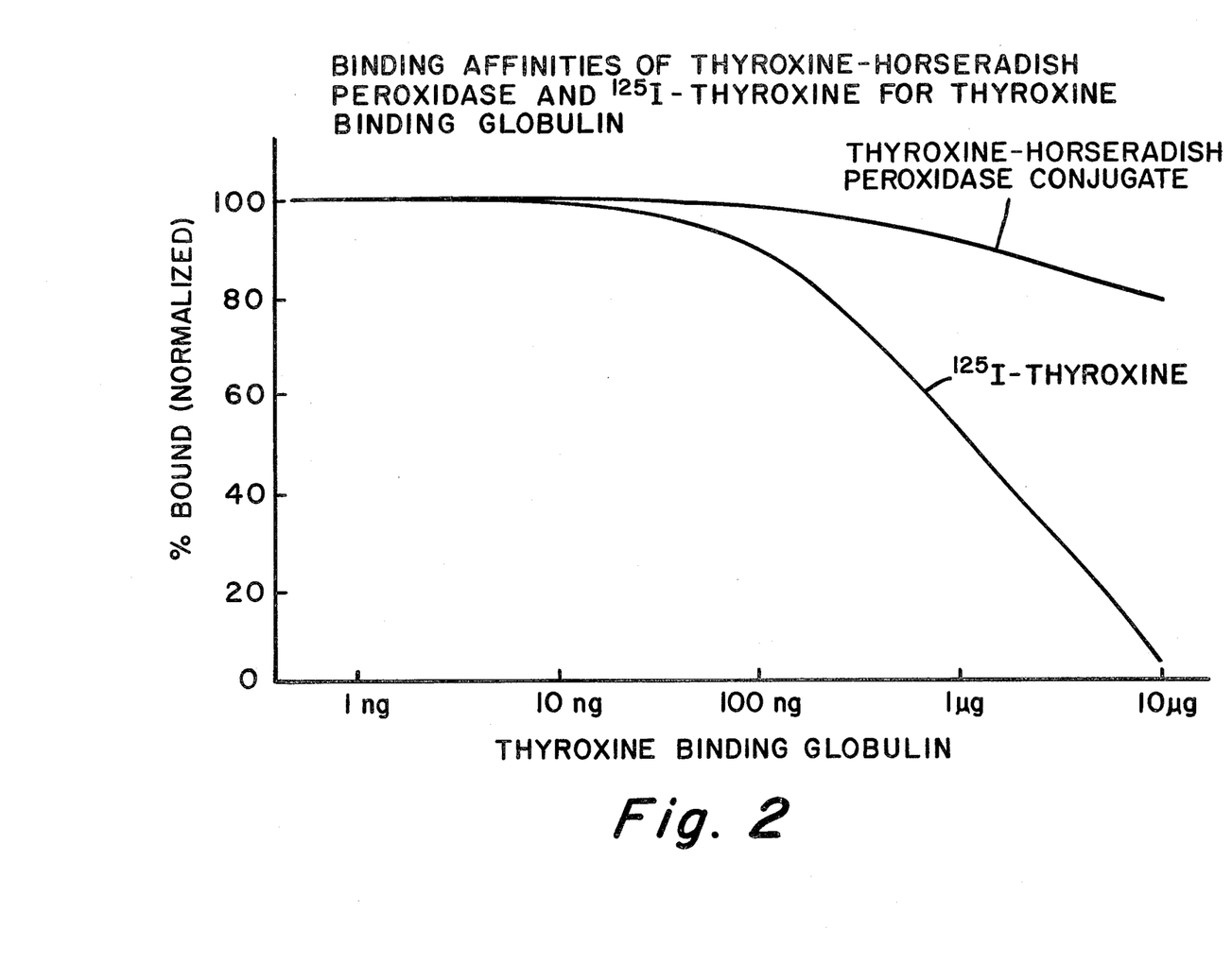
FIG. 2 demonstrates the binding affinities of thyroxine-horseradish peroxidase conjugate and $^{125}I$-thyroxine for thyroxine-binding globulin.

The two sets of data, when normalized as B/Bmax (where B represents thyroxine bound), and plotted vs. TBG concentration (FIG. 2), indicated a very low level of interaction between the conjugate and TBG as compared with the interaction of unconjugated thyroxine with TBG.

The above procedure was essentially repeated, except that the antibody suspension consisted of 400 $\mu$g. of IMA in 0.5 ml. of buffer, the series A tubes were omitted, and the TBG was replaced with thyroxine-binding prealbumin (TBPA) at concentrations of 1.28 mg./ml., 640 $\mu$g./ml., 320 $\mu$g./ml., 160 $\mu$g./ml., 80 $\mu$g./ml., and zero $\mu$g./ml., respectively, per 25-$\mu$l sample of TBPA solution which was added to each tube. Thus, the total quantity of TBPA present in each tube was, respectively, 32 mg., 16 mg., 8 mg., 4 mg., 2 mg., and zero mg.

Figure 3:
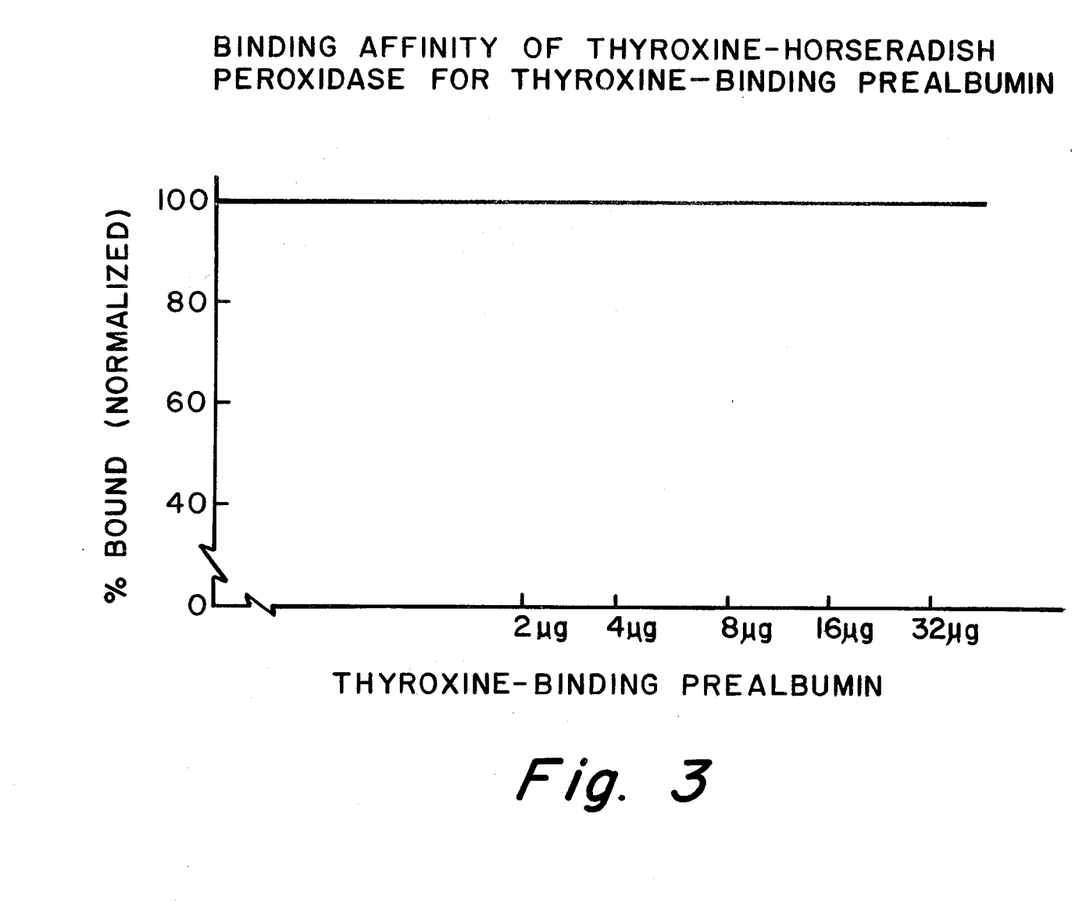
FIG. 3 demonstrates the binding affinity of thyroxine-horseradish peroxidase conjugate for thyroxine-bind prealbumin.

The data, when normalized and plotted vs. TBPA concentration, indicated virtually no interaction between the conjugate and TBPA over the concentration range studied (FIG. 3).

EXAMPLE 2

Determination of Free Thyroxine in Human Serum Samples via Enzyme Immunoassay Utilizing Antibody Immobilized in a Plastic Tube The enzyme immunoassay of Example 1 was repeated except that the antibody immmobilized on a particulate carrier was replaced with anti-thyroxine antibody-coated tubes, i.e., antibody immobilized in a plastic tube. Such tubes were obtained from Clinical Assays.

This substitution, of course, required changes in protocol whereby all centrifugation steps were eliminated with supernatant or liquid phase removal being accomplished by decantation.

Figure 4:
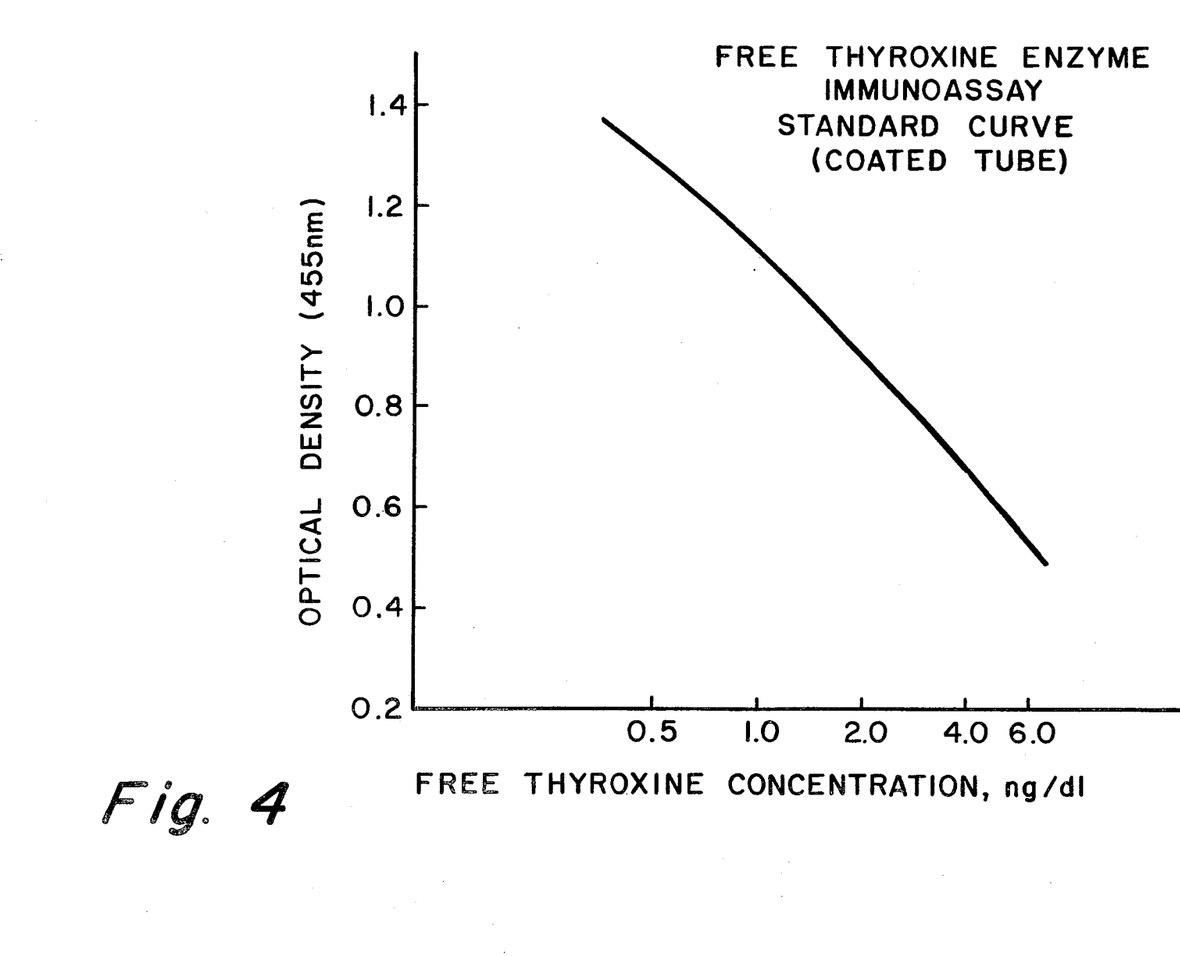
FIG. 4 is a free thyroxine enzyme immunoassay standard curve obtained with antibody immobilized in a plastic test tube.

Thus, the standard curve was generated in the usual manner by plotting optical density versus free thyroxine concentration in ng./dl. A typical standard curve is represented by FIG. 4.

The assay of human serum samples also was carried out, the data obtained being summarized in Table III which also tabulates the previously-determined free thyroxine values.

TABLE III

| Sample No. | Free Thyroxine Values of Human Serum Samples (ng./dl.) | |
|---|---|---|
| | Present Method | Prior-Art Method |
| C-10 | 0.62 | 0.98 |
| C-12 | 1.17 | 1.08 |
| M-11 | 0.39 | 0.13 |
| T-17 | 3.7 | 4.1 |

EXAMPLE 3

Preparation of Standard Curve for Radioimmunoassay

The standard curve preparation procedure of Example 1 was repeated, except that the thyroxine-horseradish peroxidase conjugate was replaced by a $^{125}$I-thyroxine-horseradish peroxidase conjugate prepared by the periodate oxidation of the enzyme followed by reaction with $^{125}$I-labeled thyroxine, following the procedure of P. K. Nekane and A. Kawaoi, *J. Histochem. Cytochem.*, 22, 1084 (1974).

The horseradish peroxidase was obtained from Worthington Biochemical Corporation, Freehold, N.J., and had a peroxidase activity of 1058 I.U./mg. Radiolabeled thyroxine, $^{125}$I-thyroxine, having an activity of about 600 μCi/μg, was supplied by Corning Medical, Medfield, Mass.

Briefly, the amine groups on the enzyme were blocked by reacting 10 mg. of horseradish peroxidase with 1 mg. of fluorescein isothiocyanate in 2 ml. of 0.3 M sodium bicarbonate solution having a pH of 8.1 for one hour at ambient temperature. Sodium perodate was added to the reaction mixture in an amount sufficient to give a concentration of about 0.01 M. The reaction then was continued for an additional 30 minutes, also at ambient temperature. To the reaction mixture then was added 1 ml. of 0.16 M ethylene glycol in distilled water; the reaction was continued at ambient temperature for one hour. The reaction mixture then was dialyzed against three four-liter changes of 0.01 M aqueous sodium carbonate solution, pH 9.5. A solution of about 50 ng $^{125}$I-thyroxine in 1 ml. of 3.0 M sodium carbonate solution at pH 8.1 was added to the dialyzed reaction mixture and the resulting solution was stirred gently at ambient temperature for 90 minutes. To the reaction solution was added 5 mg. of solid sodium borohydride and stirring was continued overnight at 4°. The $^{125}$I-thyroxine-horseradish peroxidase thus prepared was isolated by column chromatography on G-25 Sephadex (Pharmacia Fine Chemicals, Uppsala, Sweden) and stored at 4°.

Figure 5:
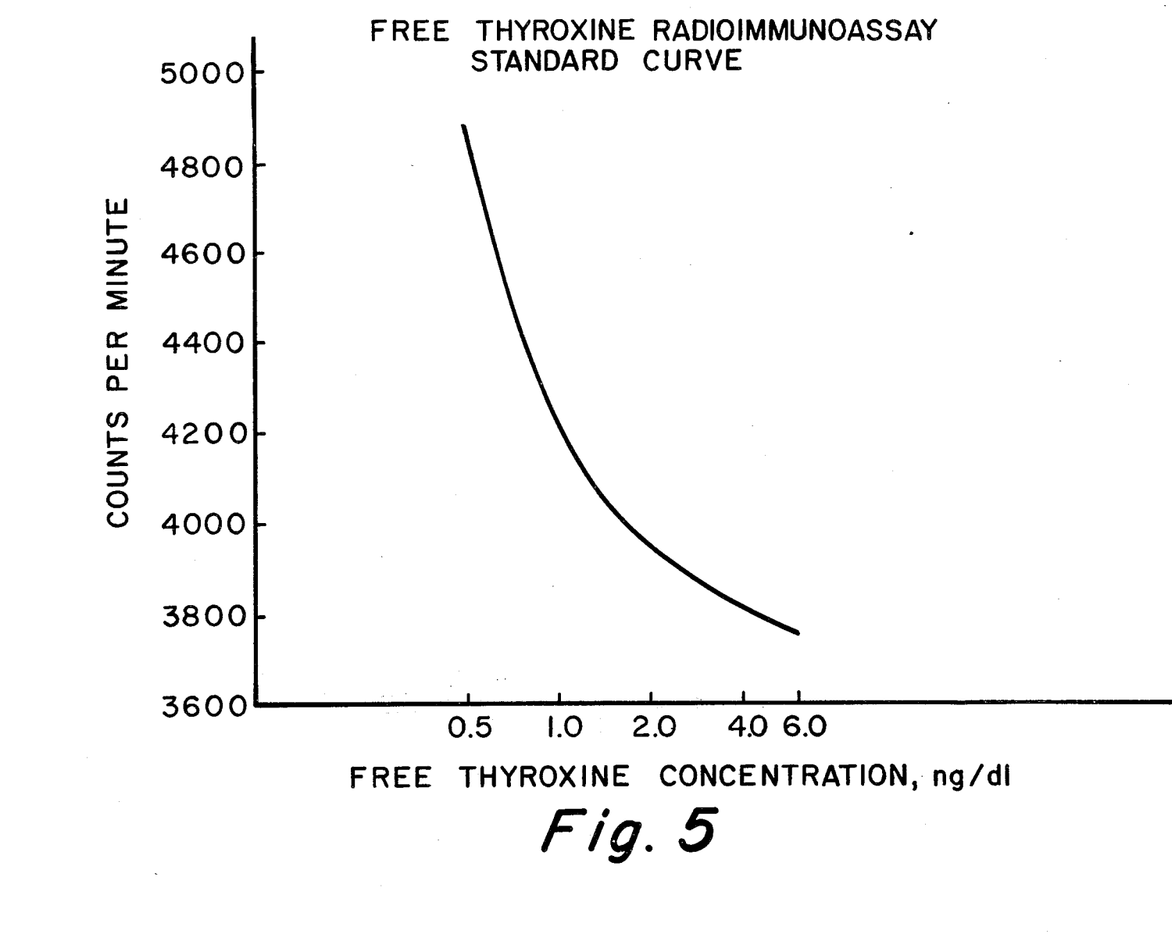
FIG. 5 is a free thyroxine radioimmunoassay standard curve.

An aliquot (50 μl) of the radiolabeled conjugate, which aliquot contained about 20,000 CPM of radioactivity, was combined with 20 μl. of each thyroxine standard, as in Example 1. Incubation was for one hour, rather than 30 minutes. As before, the solid phase was washed twice. The radioactivity bound to the solid phase then was counted for one minute. The data were plotted vs. free thyroxine concentration in ng./dl. to give a standard curve (FIG. 5).

Additional studies with the enzyme immunoassay as carried out in Example 1 demonstrated that, as expected, the preparation of the standard curve is both time and temperature dependent. If the incubation leading to complex formation is carried out at 37°, equilibrium is essentially reached after one hour. At ambient temperature, however, equilibrium apparent was not achieved after 90 minutes.

In addition, other studies demonstrated that the enzyme immunoassay as carried out in Example 1 correlated well (r=0.91) with a prior-art radioimmunoassay based on U.S. Pat. No. 4,046,870 (IMMO PHASE ™ Free Thyroxine Radioimmunoassay, Corning Medical). Such correlation resulted from the application of data from both procedures for 54 serum samples to a computerized linear regression program.

It should be apparent to one having ordinary skill in the art that many variations are possible without departing from the spirit and scope of the invention. Thus, the present invention contemplates the use of labels other than radioactive isotopes or utilization of the enzymatic activity of the horseradish peroxidase in the conjugate. As already indicated, examples of such labels include fluorescent and chemiluminescent labels. Furthermore, the present invention is not to be limited by the method of measurement.

What is claimed is:

1. An immunoassay for the direct measurement of free thyroxine in a liquid sample in which the thyroxine is present in both free and combined states, which immunoassay comprises the steps of:
   A. combining the sample with a labeled thyroxine-horseradish peroxidase conjugate which does not significantly interact with the thyroxine-binding globulin and thyroxine-binding prealbumin originally present in the sample and immobilized antibody which is specific for thyroxine;
   B. Incubating the resultant mixture;
   C. separating a solid phase from the liquid phase; and
   D. measuring the amount of labeled thyroxine-horseradish peroxidase conjugate present in either phase by means of the activity of the label;
in which the conjugate is radiolabeled, fluorescent labeled, or chemiluminescent labeled.

2. The immunoassay of claim 1 in which the conjugate is radiolabeled.

3. The immunoassay of claim 2 in which the conjugate is labeled with radioactive iodine.

4. The immunoassay of claim 3 in which the radioactive iodine is I$^{125}$.

5. The immunoassay of claim 2 in which the antibody is immobilized on an inorganic carrier.

6. The immunoassay of claim 5 in which the carrier is particulate and relatively finely divided.

7. The immunoassay of claim 6 in which the carrier is siliceous.

8. The immunoassay of claim 7 in which the carrier is glass.

9. The immunoassay of claim 2 in which the carrier is a three-dimensional article.

10. The immunoassay of claim 9 in which the carrier is a test tube.

11. The immunoassay of claim 10 in which the test tube is plastic.

12. The immunoassay of claims 9 or 10 in which the antibody is coated on the lower interior portion of the test tube.

13. An immunoassay for the measurement of free 3,5,3'-triiodothyronine in a liquid sample in which the 3,5,3'-triiodothryonine is present in both free and combined states, which immunoassay comprises the steps of:
  A. combining the sample with a radiolabeled 3,5,3'-triiodothyronine-horseradish peroxidase conjugate which does not significantly interact with the thyroxine-binding globulin and thyroxine-binding prealbumin originally present in the sample and immobilized antibody which is specific for 3,5,3'-triiodothyronine;
  B. incubating the resulting mixture;
  C. separating a solid phase from the liquid phase; and
  D. measuring the amount of labeled 3,5,3'-triiodothyronine-horseradish peroxidase conjugate present in either phase by means of the activity of the label.

14. The immunoassay of claim 13, in which the antibody is immobilized on an inorganic carrier which is particulate and relatively finely divided.

15. The immunoassay of claim 13, in which the antibody is immobilized on a carrier which is a test tube wherein the antibody is coated on the lower interior portion of the test tube.

* * * * *